(12) United States Patent
Villard et al.

(10) Patent No.: US 11,236,300 B2
(45) Date of Patent: Feb. 1, 2022

(54) MICROFLUIDIC DEVICE FOR CONTROLLING THE GEOMETRY OF LIVING BODIES

(71) Applicants: Centre National de la Recherche Scientifique (CNRS), Paris (FR); Institut Curie, Paris (FR); Sorbonne Universite, Paris (FR); Université de Paris, Paris (FR)

(72) Inventors: Catherine Villard, Paris (FR); Jean-Louis Viovy, Paris (FR); Renaud Renault, Paris (FR); Jean-Baptiste Durand, La Garenne Colombes (FR); Jean-Michel Peyrin, Paris (FR); Ivan Ferrante, Paris (FR)

(73) Assignees: Centre National de la Recherche Scientifique (CNRS), Paris (FR); Institut Curie, Paris (FR); Université de Paris, Paris (FR)

( * ) Notice: Subject to any disclaimer, the term of this patent is extended or adjusted under 35 U.S.C. 154(b) by 232 days.

(21) Appl. No.: 15/770,472

(22) PCT Filed: Oct. 21, 2016

(86) PCT No.: PCT/EP2016/075469
§ 371 (c)(1),
(2) Date: Apr. 23, 2018

(87) PCT Pub. No.: WO2017/068166
PCT Pub. Date: Apr. 27, 2017

(65) Prior Publication Data
US 2019/0055511 A1    Feb. 21, 2019

Related U.S. Application Data

(60) Provisional application No. 62/245,414, filed on Oct. 23, 2015.

(51) Int. Cl.
*C12M 1/00* (2006.01)
*B01L 3/00* (2006.01)
*C12M 3/06* (2006.01)

(52) U.S. Cl.
CPC ....... *C12M 47/04* (2013.01); *B01L 3/502761* (2013.01); *C12M 23/16* (2013.01);
(Continued)

(58) Field of Classification Search
None
See application file for complete search history.

(56) References Cited

U.S. PATENT DOCUMENTS

2006/0251698 A1  11/2006  Shen et al.
2008/0032403 A1   2/2008  Saito et al.
(Continued)

FOREIGN PATENT DOCUMENTS

EP    1013756 A1 *  6/2000  ............ C12M 23/16
GB    2472506 A     2/2011
(Continued)

OTHER PUBLICATIONS

Kleinfeld et al., Controlled outgrowth of dissociated neurons on patterned substrates, 1988, Journal of Neuroscience, 8(11), pp. 4098-4120 (Year: 1988).*

*Primary Examiner* — Holly Kipouros
(74) *Attorney, Agent, or Firm* — Banner & Witcoff, Ltd.

(57) ABSTRACT

The present invention relates to a microfluidic device to manipulate, select, treat, or cultivate living bodies, comprising a first chamber, a second chamber and a network of guiding tracks, wherein: said network of guiding tracks comprises at least one first guiding track connecting the first chamber and the second chamber and at least one second guiding track connecting said at least one first guiding track with at least two interconnections; and said at least one
(Continued)

second guiding track comprises a curved part; said curved part exhibiting a concavity facing the second chamber or the part of the network connected to the second chamber.

19 Claims, 7 Drawing Sheets

(52) U.S. Cl.
CPC . *B01L 2300/088* (2013.01); *B01L 2300/0858* (2013.01); *B01L 2400/086* (2013.01)

(56) References Cited

U.S. PATENT DOCUMENTS

| | | | | |
|---|---|---|---|---|
| 2011/0306041 | A1* | 12/2011 | Viovy | C12M 23/16 435/6.1 |
| 2014/0004557 | A1* | 1/2014 | Ma | C12M 21/06 435/29 |
| 2014/0227777 | A1* | 8/2014 | Choi | C12M 45/00 435/309.1 |

FOREIGN PATENT DOCUMENTS

| | | |
|---|---|---|
| WO | 2010/040920 A2 | 4/2010 |
| WO | 2012/166719 A1 | 12/2012 |

* cited by examiner

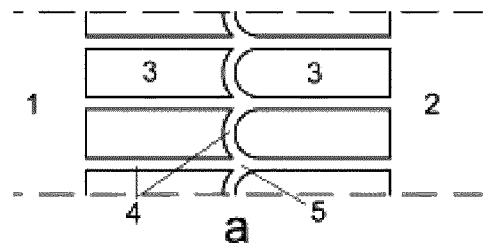
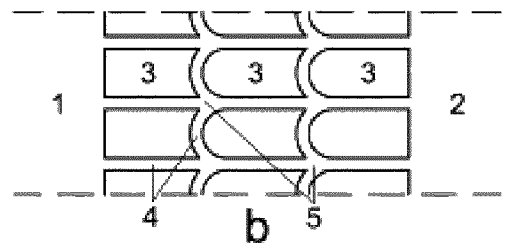
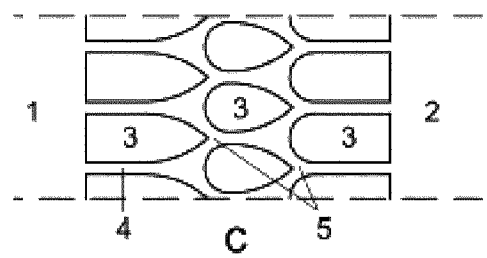
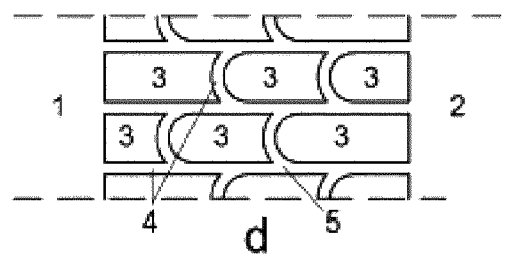
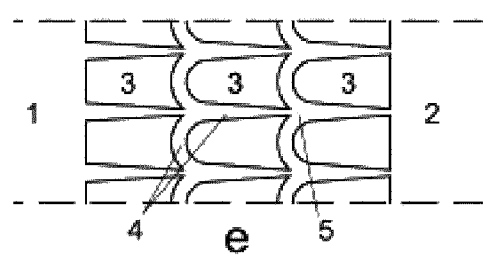
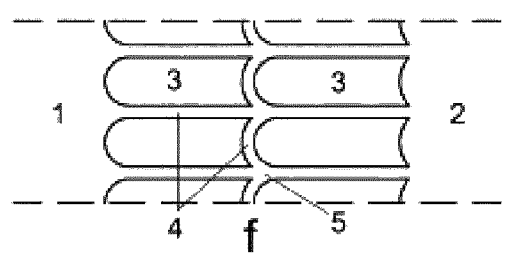
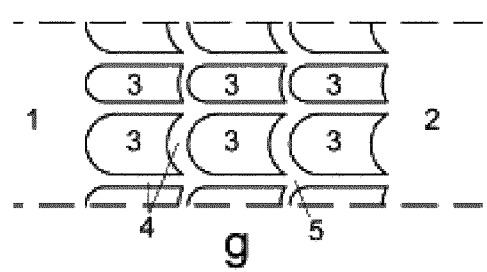
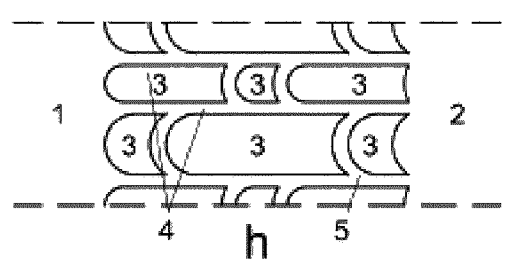
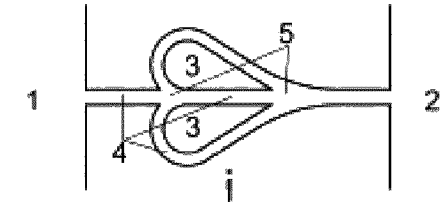
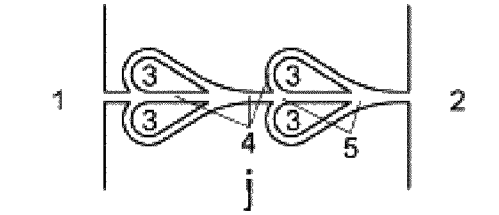
FIG. 4 (a-j)

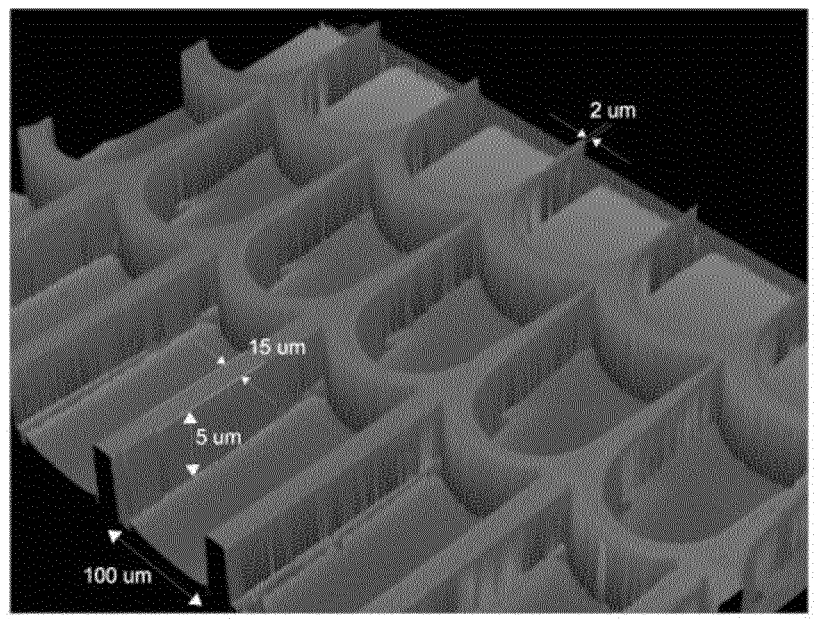
FIG. 5
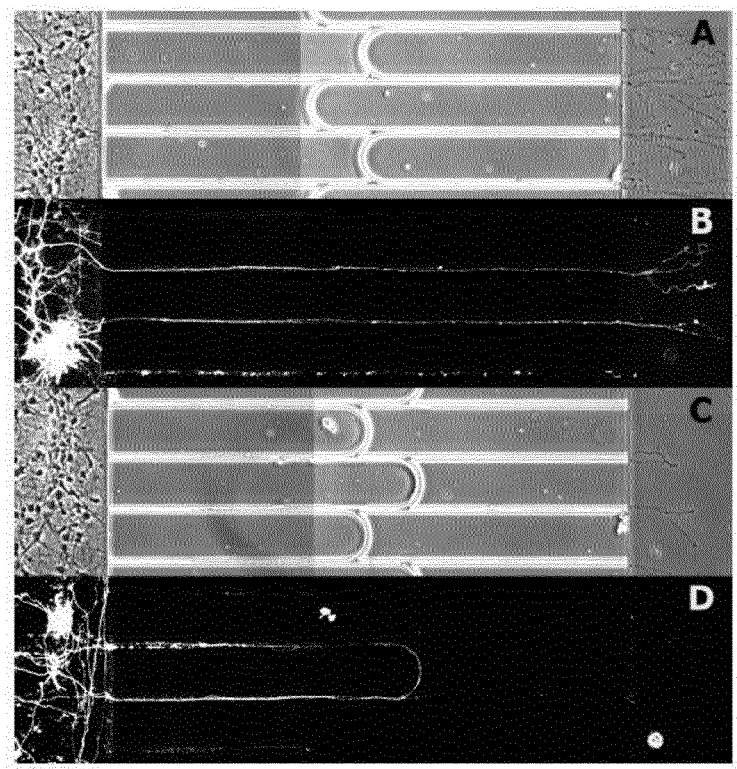
FIG. 6 (A-D)

MICROFLUIDIC DEVICE FOR CONTROLLING THE GEOMETRY OF LIVING BODIES

RELATED APPLICATION DATA

This application is a National Stage Application under 35 U.S.C. 371 of PCT application number PCT/EP2016/075469 designating the United States and filed Oct. 21, 2016; which claims the benefit of U.S. Provisional application No. 62/245,414 and filed Oct. 23, 2015 each of which are hereby incorporated by reference in their entireties.

FIELD OF INVENTION

The present invention relates to microfluidic devices and processes to cultivate cells or living bodies, in particular of neuronal cells. In some embodiments, it relates to microfluidic devices to control the shape of living bodies, or the connectivity between living bodies.

BACKGROUND OF INVENTION

Being able to cultivate in vitro various types of living bodies, notably biological neurons and any cell type that can give rise to neurons in controlled arrays will open the door to groundbreaking applications in many scientific fields. In fundamental science, this could be used to study signal processing by the brain, or brain development. In medicine, glucose-powered neural implants could repair cerebral functions. In vitro assays could also foster drug discovery and drug screening in the pharmaceutical industry. For instance cellular cultures can find applications as models to understand the cellular and molecular mechanisms at play in neuro-degenerative diseases (Alzheimer, Huntington, Creutzfeldt-Jakob, etc.), or after brain injury, and to study the effect of molecules or drugs on these mechanisms. Finally, biological information processors could lead to new kinds of artificial intelligence.

Various experimental models are used for the above applications. A first family of models use electrical recording or imaging in whole animal models. The anatomical structures are intact but experimentation at the cellular level is severely restricted. A second family of models use brain slices, or more generally tissue slices. In this case, high resolution imaging and mechanical or chemical addressing are easier than in whole animals, but the lifetime of such cultures is short, and it is very difficult to keep knowledge of the physical connectivity of individual neurons, in a dense 3D array. Also, in order to perform high resolution imaging, and feed correctly a living tissue disconnected from its natural vascular system, very thin slices must be made, so the real 3D architecture is strongly perturbed, and many neuronal connections are lost. Finally, dissociated cultures in petri dishes or wells of microtiter plates are widely used. They have many advantages above: neurons can be cultivated for at least several weeks; high resolution imaging and recent biological staining methods can be used. Also, in principle and at low density at least, individual neurites can be followed. In these systems, however, cell development and connection is spatially random, making these systems very different from real ones in terms of cell-cell transactions and functionality.

Several attempts have been made to overcome the above limitations. For instance, in WO 200434016, or in WO 2006037033 and U.S. Pat. No. 7,419,822, Jeon et al., inspired by work of Campenot [Campenot, R. B. Local control of neurite development by nerve growth Factor. Proc. Natl. Acad. Sci. The USA. 1977, 74 (10), 4516-4519], propose a microfluidic device allowing insulation of the soma from the neurons of their axon. This involves a first chamber, in which neurons are seeded, a multiplicity of microchannels in which neurites, but not cell soma, can enter, and a second chamber, in fluidic connection with said first chamber by means of the microchannels.

This device is a first step towards the control of the neuronal cultures of in vitro central nervous system (CNS) axons in vitro. Times of diffusion in the microchannels are long, which makes it possible to treat in a different way the content of said first and second chambers. However, this device still presents many limitations. First, it makes it possible to separate the cellular compartments, but, if two populations are seeded in first and second chamber, it does not allow control of the direction of the connection of axons, thus making the connection not physiological.

In WO 2010/040920, Peyrin et al. proposed a solution to the first problem, thanks to a device of culture, in particular of neuronal cells, including: a support defining a first room microfluidics intended to be sown by a first cellular culture, and at least a second room microfluidics, a system of fluidic interconnection (3) connecting the first and second room and allowing cellular extensions, in particular axons, to extend from a room towards the other room. In said device, the system of interconnection is carried out so as to privilege the progression of at least a first type of cellular extensions compared to at least a second type of cellular extensions, the aforementioned extensions first and second types of cellular extensions differing either by the microfluidics room whose they come from, or by the cellular type of which they are the extension. This effect, however, requires the fabrication of narrow channels, which has two disadvantages. First, the fabrication is delicate and leads to some irreproducibility. Second, said narrow channels can be easily clogged by axons themselves, leading to irreproducibility and variations of fluidic connection during cell culture. Finally, the selectivity is not 100%, as demonstrated e.g. in Peyrin et al. [Lab Chip. 2011 Nov. 7; 11(21):3663-73. doi: 10.1039/c11c20014c].

In Lab Chip. 2013; 13(4): 589-598. doi:10.1039/c21c41000a, Honegger et al. describe three dimensional topological networks of neuron based on AC electrokinetic confinement. Said confinement adds flexibility to the design of neuronal arrays, but it requires complex chips with integrated electrodes, and complex control electronics.

There is thus a strong need for improved artificial systems and methods to guide neurites, or more generally to control cell shapes and protrusions.

RESUME

The present invention relates to a microfluidic device to manipulate, select, treat, or cultivate living bodies, comprising a first chamber, a second chamber and a network of guiding tracks, wherein:
  said network comprises at least one first guiding track connecting the first chamber and the second chamber and at least one second guiding track connecting said at least one first guiding track with at least two interconnections; and
  said at least one second guiding track comprising a curved part; said curved part exhibiting a concavity facing the second chamber or the part of the network connected to the second chamber.

According to one embodiment, said network of guiding tracks comprises at least two first guiding tracks connecting the first chamber and the second chamber and wherein each first guiding track comprises at least one interconnection with the at least one second guiding track.

According to one embodiment, each first guiding track comprises at least two interconnections with the at least one second guiding track.

According to one embodiment, the network of guiding tracks comprises at least two second guiding tracks wherein each second guiding track connects the at least one first guiding track with at least two interconnections.

According to one embodiment, each first guiding track is connected to at least two second guiding tracks.

According to one embodiment, each interconnection is a 3-way interconnection.

According to one embodiment, the internal angle facing the second chamber or the part of the network connected to the second chamber between the at least one first guiding track and the at least one second guiding track is ranging from 90° to 180°, from 100° to 180°, from 120° to 180°, from 150° to 180°, from 160° to 180° or from 170° to 180°.

According to one embodiment, the internal angle facing the first chamber or the part of the network connected to the first chamber between the at least one first guiding track and the at least one second guiding track is smaller than 150°, 140°, 130°, 120°, 110°, 100° or 90°.

According to one embodiment, the space between two adjacent interconnections along one first guiding track ranges from 20 μm to 5 mm.

According to one embodiment, areas or volumes on the device of the invention not being part of any guiding track nor of chambers, are repellent areas or repellent volumes; said repellent areas or repellent volumes present an ability to support the growth or adhesion of living bodies, lower than the ability to support the growth or adhesion of cells of guiding tracks or chambers.

The present invention also relates to a microfluidic device comprising at least one first chamber and at least one second chamber connected by at least one first guiding track, wherein the at least one first chamber and the at least one second chamber comprise both a bottom and wherein:
the at least one first guiding track is connected to the at least one first chamber at the level of the bottom of the at least one first chamber; and
the at least one first guiding track is connected to the at least one second chamber at a level higher than the level of the bottom of the at least one second chamber so as to design a step between the bottom of the at least one second chamber and the at least one first guiding track.

According to one embodiment, the microfluidic device according to the present invention further comprises at least one third chamber connected to the at least one second chamber by at least one second guiding track.

According to one embodiment, the guiding tracks comprise one or several micro-cut on at least one of their surface.

According to one embodiment, the at least one third chamber comprises a bottom and:
the at least one second guiding track is connected to the at least one second chamber at the level of the bottom of the at least one second chamber; and
the at least one second guiding track is connected to the at least one third chamber at a level higher than the level of the bottom of the at least one third chamber so as to design a step between the bottom of the at least one third chamber and the at least one second guiding track.

According to one embodiment, the bottom of the at least one second chamber is not parallel with the bottom of the at least one first chamber.

The invention also relates to a method to manipulate, select, treat, or cultivate living bodies, comprising the following steps:
providing a microfluidic device according to the present invention;
cultivating at least one living body in the at least one first chamber and cultivate at least one living body in the at least one second chamber;
guiding at least one living body from the at least one second chamber to the at least one first chamber without guiding the at least one living body from the at least one first chamber to the at least one second chamber.

The invention also relates to a method to manipulate, select, treat, or cultivate living bodies, comprising the following steps:
providing a microfluidic device according to the present invention;
cultivating at least one living body in the at least one first chamber and cultivate at least one living body in the at least one second chamber;
guiding at least one living body from the at least one second chamber to the at least one first chamber and avoiding in the same time the at least one living body in the at least one second chamber to reach the at least one first chamber.

According to one embodiment, living bodies are cells, neurites, axons, dendrites, invadopodia, filipodia, cell membranes, cellular protrusions, flagella, microtentacles, growth cones, glial cells, fungi, plant cells, filamentous fungies, whole organisms, worms, yeasts, myxomycetes, animal cells, multicellular spheroids, organoids, or embryos.

Definitions

In the present invention, the following terms have the following meanings:
By "Channel", we mean any elongated space, tube, duct, pipe, conduit, along which a fluid substance can be transported. More specifically, we designate channels as microchannels if they are micrometric, i.e. if at least one dimension of their section is comprised between 1 μm and 1 mm, as millichannels if they are millimetric, i.e. if at least one dimension of their section is comprised between 1 mm and 1 cm, or as nanochannels if they are nanometric, i.e. if at least one dimension of their section is comprised between 1 nm and 1 μm.
"Minichannels", In many preferred embodiments, the invention is particularly interesting for microchannels. However, for the sake of terseness and completeness, in the following we shall design as minichannels channels that comprise along their length at least a portion that is either millimetric, micrometric, or nanometric.
By "Minifluidic chip", or more tersely "chip", or "minifluidic component", or "minifluidic device", we designate an object comprising at least one channel, or at least one combination of channels, said channel or combination of channels being embedded at least in part in a matrix. Preferably, said channels are minichannels. However, for the sake of simplicity, except when specified otherwise, in the following we shall also encompass in the designation "minifluidic" objects that are either microfluidic, i.e. comprise at least one microchannel, millifluidic, e.g. comprise at least one millichannel, or nanofluidic, i.e. comprise at least one nanochannel, or chips comprising any combination of millichannels, nanochannels or microchannels.

By "Chamber", we designate in some embodiments a channel, or a part of a channel, with one dimension, called the "thickness", significantly smaller than the two other dimensions. Such chambers can be millichambers, microchambers, or nanochambers, if at least one of the other dimensions is millimetric, micrometric, or nanometric, respectively. Millichambers, microchambers, and nanochambers are encompassed under the common name of "minichambers". Typically, chambers in the invention are intended to be able to contain a larger volume of fluid by unit length, than the channel with which they are in fluidic connection. Thus, in some embodiments, chambers may also be as a volume defined inside a device, or as a recess on top of a device, and having at least one lateral dimension larger than the smallest lateral dimension of a channel to which it is in fluidic connection. In some preferred embodiments, said one lateral dimension of the chamber, is smaller than all lateral dimensions of said channel.

By "Instrument", we designate an integrated device that is able to perform at least one function without the addition of additional components other than components available in the operational environment, such as for instance an energy source, or consumables. In our description, instruments are thus a subcategory of integrated device.

By "Device", we designate any of a chip, a component, an instrument, or a system.

By "System", we designate a combination of instruments associated to exert one or several tasks.

By "Minifluidic device", (resp. Microfluidic, millifluidic, nanofluidic), we designate a device comprising at least one minichannel (resp. Microchannel, Millichannel, Nanochannel), but optionally comprising other components, said other components not necessarily fluidic or minifluidic in their nature or function. Minifluidic devices of the invention may involve different levels of integration. For instance, they can be restricted to a single minifluidic chip or component, integrating one or several functionalities. Minifluidic devices of the invention may also comprise all other kinds of elements and components, some of which explicitly described here, such as pumps, valves, sensors, actuators, detectors, and many others known in the art, which are encompassed within the field of the invention. In particular, minifluidic devices of the invention may also be full instruments, and integrate for instance any of holders, housings, power sources, control software and hardware, communication means, storage means, manipulation means, human-machine interfaces.

By the term "Integrated device", we designate a device comprising a minifluidic chip or component of the invention, and at least one additional component.

By "Additional component", we designate components that are not integral part of the minifluidic chip or minifluidic device of the invention, but may be necessary or advantageous for operating the invention, or for exerting some advantages of the invention. Said components may comprise for instance mechanical manipulators or holders, fluid containers, ducts or mobilization means, electric components or optical components or information treatment components, user interfaces, housings, and the like. As a common characteristic, additional components of the invention are in connection or in relation with the invention's minifluidic device or minifluidic channel by some means, for instance mechanical, electrical, electomagnetic, optical, fluidic, and are involved in at least one potential way of operation of the invention's device.

By "Living bodies", we designate living organisms, living parts of organisms, living cells, or living cellular assemblies. This includes for instance organs, parts of organs, cells, cellular assemblies, from various organisms including humans, notably biological neurons and any cell type that can gives rise to neurons.

By "Guiding track", we designate a specific area, within a minifluidic device, in which, or onto which, living bodies of interest will have a preference for their positioning, or growth, as compared to parts of said device not belonging to the guiding track. Said guiding track may be chemical, for instance defined by some specific chemicals on a surface or in the bulk of a liquid or in a gel, or some specific chemical property, such as a charge, a pH, a hydrophobicity, a chemical composition; it can also be biological or biochemical, for instance defined by some specific biological or chemical species, such as proteins, antibodies, aptamers, affybodies, cells, and the like. Said guiding track may also be physical, i.e. it may consist in areas comprising, or surrounded by, topological structures such as microstructures, nanopillars, micropillars, nanopillars, walls. In such case, they may thus be channels, trenches, wedges, chambers; guiding tracks may also involve other types of guidance cues, such as areas with temperatures, or radiation, or light illumination, different from the rest of the device. Guiding tracks as defined here have two extremities. Preferably, said extremities are interconnections, either with at least one of another guiding track, or a chamber. Guiding tracks in the invention may be of any size, nanometric, micrometric, millimetric. Preferably, at least some guiding tracks in the invention are elongated.

By "Traversing guiding tracks", we designate guiding tracks connecting two adjacent guiding tracks; said adjacent guiding tracks connect a first chamber to a second chamber. Said traversing guiding tracks comprise a curved part exhibiting a concavity wherein said concavity of said curved part is facing the first chamber which is a receiving chamber.

By oppositions, areas on a device of the invention not being part of any guiding track, or of chambers, are named "Repellent areas". This is to be intended in a broad sense, i.e. encompassing not only surfaces treated to repel cells, but any area presenting an ability to support the growth or adhesion of cells or cell protrusions, lower than the ability of guiding tracks. For instance, "repellent areas" may be areas with no surface treatment, or areas with a hydrophilic, preferably uncharged, nature, or elevated topographical structures, or areas in the volume of the material constituting the device, in which cells cannot penetrate, and the like . . . .

Also, devices of the invention generally have an extension in 3 dimensions, typically because cells or more generally living bodies are tridimensional and thus need some thickness to grow. Thus, the notion of "repellent areas" in the invention is defined with respect to a plane, notwithstanding the fact that this plane can be only a cut across a repelling zone that is indeed a volume. Thus "repellent areas" and "repellent volumes" will be used equivalently in the description. For instance, the presence of an asymmetry in "cusps", or curved zones and so on, and more generally the structures that characterize the invention, may involve different types of cuts, along different types of planes, depending on the embodiment.

For instance, many embodiments are organized along a planar design, and the cusps or other structures, are also organized along said plane. This is for instance the case in the embodiments described in FIG. 3. Some other embodiments may take advantage of the third dimension to implement the invention. This is for instance the case of the embodiments presented in FIG. 8. In that case, the concept of "repellent areas", or "cusps", are to be considered along a plane different from the main plane of the device, for instance in the case of FIG. 8, a perpendicular cut along the BB' plane.

"Interconnected channels", or "Interconnected guiding tracks", as used herein, refers to two or more channels or tracks within the structure that are in contact at at least one extremity.

A place at which two guiding tracks encounter each other is called an "Interconnection". Interconnections may involve a different number of guiding tracts or channels. For instance, FIG. 4*a* displays an interconnection involving 4 guiding tracks, or "4-ways interconnection"; FIG. 4*d* shows an interconnection 5 involving 3 guiding tracks, or "3-ways interconnection".

An interconnected network is said to comprise "Multiple interconnections", if it comprises at least two distinct interconnections, or at least one interconnection involving at least 4 guiding tracks.

A channel, or a multiplicity of non-connected or interconnected channels or guiding tracks, define in the device one or several "Flow paths" or guiding paths, i.e. paths that a fluid can follow under the action of external forces, or under the action of diffusion, or, respectively, paths that cells or cell.

We designate as a "Network" of channels or guiding tracks, an ensemble of channels or guiding tracks, each of which comprises at least a fluidic connection with a second channel or guiding track in said network or a contact with another guiding track of said network. Said network is called an "interconnected network", if a fluidic flow path, or a continuity along guiding tracks, can be found between any two channels or any two guiding tracks in said network.

By "Sharp angle", or "Cusp", referring to the boundary of a guiding track, or to a guiding track, we designate a location at which said boundary or said track changes orientation abruptly. Abruptly should be understood in reference to the possibilities of the microfabrication means used to prepare the device, and to the properties of the living bodies present on said guiding track. For instance, many fabrication techniques have a limited resolution, so angles with a radius of gyration smaller than said resolution, or smaller than said resolution multiplied by some numerical factor, cannot be made. Thus an angle with some rounding limited by fabrication resolution will still be considered as sharp within the invention. Also, regarding the living bodies, an angle will be considered as "sharp", if its radius of gyration is smaller than the turns that said living bodies are able to take without damage, possibly multiplied by a factor.

By opposition, we define as a "Curved" part of a guiding track, a zone along a guiding track, along which the main axis of said guiding track has an orientation that changes progressively. Similarly, we define as "curved" the boundary of a guiding track, or of a repellent zone, if the orientation of said boundary changes progressively. In some embodiments, a location on a boundary of a guiding track will be defined as a "cusp", if the radius of gyration of said boundary, at said location, is smaller than 2 times, preferably smaller than 5 times, or 10 times, the radius of gyration of said boundary on either side of said location.

Also in some embodiments, a part of a guiding track will be defined as curved, if the radius of gyration of the main axis of said guiding track, is finite but larger than 2 times, preferably larger than 5 times, or 10 times, the width of said guiding track.

In some embodiments, a location on a boundary of a guiding track will be defined as a "cusp", if the radius of gyration of said boundary, at said location, is smaller than 2 times, preferably smaller than 5 times, or 10 times, the radius of gyration of said boundary on either side of said location; equivalently, one can define in some embodiments a "cusp", as a place where the inverse of the radius of gyration of the structure's boundary has a peak that is at least 2 times, preferably 5, 10, or 20 times, higher than the value of said inverse on each side of said peak.

In some embodiments, said cusp may also be defined in reference to the properties of the cells, or of the cell protrusions, to be guided. For instance, a place along boundary of a cell guiding structure will constitute a "cusp", if the radius of gyration of said boundary at said location is smaller than the persistence length or typical curvature of the guided cellular structures, preferably smaller than 2, 5, 10, 20 or 50 times said persistence length or typical curvature. In some embodiments, said cellular structures are cell protrusions.

Oppositely, a zone along a guiding track will be defined as "curved", if its main axis is not linear, and has a radius of gyration larger than the persistence length or typical curvature of the guided cellular structures, preferably larger than 2, 5, 10, 20 or 50 times said persistence length or typical curvature.

Said "Cell protrusions" may be any part of a cell protruding from the soma, for instance neurites, or axons, or dendrites, or invadopodia or filipodia, or cell membranes, or cellular protrusions, or flagella, or microtentacles, or growth cones.

To fix ideas, in the case of neurons, for instance, a place along a boundary will be considered as a cusp, if its radius of gyration is smaller than 2 micrometers, or smaller than 5, 8, 10 or 20 µm.

Importantly too, a cusp defines an angle of change of orientation, between the orientation of the boundary on one side of said cusp, and the orientation of the boundary on the other side of said cusp.

DETAILED DESCRIPTION

The invention pertains to the domain of minifluidics, and particularly microfluidics and nanofluidics.

More specifically, it proposes minifluidic devices to manipulate, grow, select, treat, or cultivate living bodies.

In some specific embodiments the invention proposes new ways to control the guidance, connection, or positioning, of organisms, cells, cell ensembles, cell protrusions, cell organelles, cell protrusions, cell boundaries, neurites, neurons, dendrites, cell processes, lamellipodia, invadopodia, cell extensions, and the like, said ways being more efficient or more convenient than in prior art.

In a first aspect, the invention relates to a minifluidic devices to manipulate, grow, select, treat, or cultivate living bodies, comprising at least a first chamber, called "emitting chamber", a second chamber, called "receiving chamber", and a network of guiding tracks with at least two interconnections, said network defining between at least some of its elements repellent areas surrounded by a perimeter, wherein at least some of said repellent areas present, on their side in contact with the emitting chamber or with guiding tracks arising from the emitting chamber, more cusps, or cusps with a smaller angle, or a combination thereof, than on their side in contact with the receiving chamber or with guiding tracks arising from the receiving chamber.

As another aspect of the invention, it proposes minifluidic devices to manipulate, grow, select, treat, or cultivate living bodies, comprising at least a first chamber, called "emitting chamber", a second chamber, called "receiving chamber", and a network of guiding tracks with at least two interconnections, said network defining between its elements repellent areas or repelling volumes said repellent areas being limited by a perimeter, or said repelling volumes being limited by a surface, wherein at least some of said repellent areas present an asymmetry regarding the presence of curvature or cusps along the two sides of their perimeter or surface, respectively in contact with the emitting chamber, or from guiding tracks arising from the emitting chamber, and in contact with the receiving chamber, or guiding tracks arising from the receiving chamber.

As yet another aspect of the invention, it proposes minifluidic devices to manipulate, grow, select, treat, or cultivate living bodies, comprising at least a first chamber, called "emitting chamber", a second chamber, called "receiving chamber", and a network of guiding tracks with at least two interconnections, said network comprising at least traversing guiding tracks comprising at least some curved parts, wherein the concavity of said curvature preferably facing the receiving chamber, or the part of the network connected to the receiving chamber, and the convexity of said curved part preferably facing the emitting chamber, or the part of the network connected to the emitting chamber.

According to a preferred embodiment, said interconnections are 3-ways interconnections. In another embodiment, said interconnections are 4-ways interconnections.

According to one embodiment, said network of guiding tracks comprises at least 3, 4, 5, or 6 interconnections along each guiding track.

According to one embodiment, the radius of gyration of the curved part of the at least one traversing guiding track is smaller than 20 µm. In one other embodiment, the radius of gyration of the curved part of at least one traversing guiding track is smaller than 10 µm, 8 µm, 5 µm, or smaller than 2 µm. This radius of gyration allows the living bodies to change of orientation and leave the guiding track connecting the two chambers.

As yet another aspect of the invention, it proposes minifluidic devices to manipulate, grow, select, treat, or cultivate living bodies, comprising at least a first chamber, called "emitting chamber", a second chamber, called "receiving chamber", and a network of guiding tracks said guiding tracks presenting more cusps, or more acute cusps, on their side facing the receiving chamber, or on their side in contact with the part of the network connected to the receiving chamber, than on their side facing the emitting chamber, or on their side in contact with the part of the network connected to the emitting chamber comprising at least some curved parts, wherein the concavity of said curvature preferably facing the receiving chamber, or the part of the network connected to the receiving chamber, and the convexity of said curved part preferably facing the emitting chamber, or the part of the network connected to the emitting chamber.

In some preferred embodiments, exemplified for instance in FIGS. 8b and c, at least some guiding tracks have the form of a minichannel, and the connection of said minichannel with the receiving chamber occurs on a side wall of said chamber at a position distant from the bottom of said chamber, whereas the connection of said minichannel with the emitting chamber occurs on a side wall of said chamber at a position level with from the bottom of said chamber.

In some preferred embodiments, advantageously combined with the above, the bottom of said chambers is adhesive for living bodies, whereas the side walls of said chambers are non-adhesive or less adhesive for living bodies.

By "preferably", in the description above and below, we mean that, in a global or statistical sense, there are more guiding tracks with a first property than a second property, or a given guiding track has more sections along its length, with said first property than with said second property, or a first combination of number of guiding tracks with said first property and the length of said guiding tracks with said first property is higher than a second combination established regarding to the second property. For instance, and in a non-exclusive way just given here to fix ideas, said first combination may be the sum of all the lengths of guiding tracks with a curvature having its concavity facing the receiving chamber, and said second combination may be the sum of all the lengths of guiding tracks with a curvature having its concavity facing the emitting chamber.

In some preferred embodiments, said network presents multiple interconnections.

In some preferred embodiments, said multiple interconnections present at least a 4-ways interconnection.

In some preferred embodiments, said interconnections are distributed as a one-dimensional array, or as a two-dimensional array, or as a three-dimensional array. For instance, FIG. 4a-h present interconnections distributed in a two-dimensional array, with repellent areas and connecting tracks organized in multiple columns and lines, whereas FIG. 4i-j present interconnections distributed in a one-dimensional array, as a connected lines of elementary designs. By associating as multiple layers designs as in FIG. 4a-h, one can obtain a three-dimensional array. By associating designs as in FIG. 4i-j as multiple layers, or as parallel lines on the same layer, one can obtain a two-dimensional array. In the particular representation of the figure, one uses the convention of designing columns multiple elements along the bottom-up direction, lines as multiple elements along the left-right direction, and layers in a plane perpendicular to the paper. However, this convention is only a facility of representation.

With such designs, as demonstrated for instance in examples 2 or 4, cell protrusions propagating from the emitting chamber tend to follow the rounded side of the guiding structure, and thus return to the receiving chamber. For protrusions coming from the other side, in contrast, they seem to be unable to follow said side, and thus continue towards the receiving chamber. This effect depends on the shape of the channels, guiding structures, and repellent areas, and also on the nature of the living bodies, and of the protrusion. The invention thus proposes different ways to prepare devices, which may be more useful for different types of living bodies, and/or different types of cell protrusions.

In some preferred embodiments, said network is a connected network.

In some preferred embodiments, said network, or at least some of said guiding tracks, has on at least part of their surface properties favoring cell adhesion or cell growth, or more generally an affinity for living bodies.

In some other preferred embodiments, chambers or channels of the invention, present on at least one the elements of surface limiting them, adhesive properties for living bodies, and on at least another element of surface limiting them, properties non adhesive or less adhesive, for living bodies, notably living bodies contained in said chambers or channels or to be inserted or cultivated in said chambers or channels.

Numerous ways to favor cell adhesion are known by these skilled in the art. This may consist for instance in surface with a global positive charge, for instance and not limitatively, laminin, fibronectin, poly-lysine, or more generally polymers comprising amine functions, or polymers comprising cationic moieties. This may also consist in surfaces bearing biopolymers or proteins or media favoring cell adhesion or cell growth, such as matrigel, collagen. This may also consist in surfaces with some hydrophobic properties, as commonly used in cell culture dishes, such as polystyrene.

Preferably, too, repellent areas have properties not favoring cell adhesion or cell growth, or no affinity for living bodies, or favouring cell adhesion or cell growth less than the guiding tracks, or having an affinity for living bodies less that the affinity of guiding tracks. For instance, "repellent areas" may be areas with no surface treatment, or areas with a hydrophilic, preferably uncharged, nature, or areas bearing fluorinated polymers, or elevated topographical structures, or areas in the volume of the material constituting the device, in which cells cannot penetrate, and the like . . . .

In some preferred embodiments, said connected network has a multiplicity of connections with the emitting chamber, or a multiplicity of connections with the receiving chamber, or yet preferably a combination of the above.

In preferred embodiments, the side of repellent areas in contact with guiding tracks arising from the emitting (resp. receiving) chamber is also facing said emitting (resp. receiving) chamber. In other embodiments, however, for instance if the network of guiding tracks has a contorted shape that changes the general direction of propagation of cell protrusions, this may not be the case.

Connections of the network of guiding tracks with the chambers may be of different types. For instance they may be a fluidic connection, if guiding tracks are microchannels, but if guiding tracks consist in, or comprise, a cell-adhesive surface treatment, said connections may also be a mere continuity of said surface treatment with a cell adhesive surface treatment of said chambers.

In some embodiments, at least some of the cusps of repelling areas facing, or connected to, the emitting chambers have a tip angle smaller than 150°, preferably smaller than 140°, or 130°, or 120°, or 110°, or 100°, or even more preferably smaller than 90°.

In some other embodiments, the repelling areas facing, or connected to, the receiving chambers, do not have any cusp with a tip angle smaller than 90°. Preferably the repelling areas facing, or connected to, the receiving chambers, do not have any cusp with a tip angle smaller than 96°, 100°, 120°, 150°, 154°, 160° or 170°.

In some embodiments, the repelling areas facing, or connected to, the receiving chambers, have a tip angle ranging from 90° to 180°, from 96° to 180°, from 100° to 180°, from 120° to 180°, from 150° to 180°, from 154° to 180°, from 160° to 180° or from 170° to 180°.

In some embodiment, the guiding tracks define a change in edge direction. This change of direction is defined as positive for convex corner. In one embodiment, the at least one first guiding track interconnected to the at least one second guiding track and directed to the first chamber exhibits at the interconnection a change of direction from +90° to −90°, from +84° to −84°, from +80° to −80°, from +70° to −70°, from +60° to −60°, from +50° to −50°, from +40° to −40°, from +30° to −30°, from +26° to −26°, from +20° to −20° or from +10° to −10°.

In preferred embodiments, said guiding tracks present an affinity for at least some living bodies, higher than the affinity of areas of the device not part of said guiding tracks.

In preferred embodiments, at least part of said emitting chamber or receiving chamber presents an affinity for at least some living bodies, higher than the affinity of areas of the device not part of said guiding tracks.

Another convenient way to design devices of the invention is to shape some guiding tracks part of the network connecting the emitting and the receiving chamber, in the form of arches, with their concavity facing the receiving chamber. Examples of such designs are represented in FIGS. 3b, 4, 5, 6 and 7b. By arches, we typically mean a channel or guiding track with a non-linear shape, globally presenting a concavity towards one side, and a convexity towards the other side. Said arch can have a regular radius, but it may also present more complex shapes, provided the general properties stated above regarding convexity are conserved.

Another convenient way to design devices of the present invention is to shape some guiding tracks connecting the emitting chamber and the receiving chamber, and some traversing guiding tracks connecting two adjacent guiding tracks. The traversing guiding tracks comprise at least a curved part which exhibits a concavity and a convexity, wherein the concavity of said curved part is facing the emitting chamber and the convexity of said curved part is facing the receiving chamber.

This design of the present invention allows the living bodies cultivated in the emitting chamber to be guided to the receiving chamber but does not allow the living bodies cultivated in the receiving chamber to be guided to the emitting chamber.

It is thus another object of the invention, to propose a minifluidic devices to manipulate, grow, select, treat, or cultivate living bodies, comprising at least a first chamber, called "emitting chamber", a second chamber, called "receiving chamber", and a connected network of guiding tracks with a multiplicity of connections with each of said chambers, wherein at least some of said guiding tracks have on at least part of their length the shape of arches with their concavity in the direction of the receiving chamber.

A yet other way to design devices of the invention is to shape some repellent areas in the form of rounded tiles, with the convex part facing the emitting chamber. An example of such design is presented in FIG. 4.

It is thus another object of the invention, to propose a minifluidic devices to manipulate, grow, select, treat, or cultivate living bodies, comprising at least a first chamber, called "emitting chamber", a second chamber, called "receiving chamber", and a connected network of guiding tracks defining between them repellent areas, wherein some of said repellent areas have the form of rounded tiles with their convex part facing the emitting chamber.

In many cases, it will be easy for those skilled in the art of microfluidics, or in the art of cell culture, to design devices of the invention with the above definitions. It is, however, another object of the invention, to provide additional ways to help users in such design, for instance by the use of some qualitative rules, or by some algorithms or mathematical formula useful in optimizing the shape of repellent areas. An example of algorithm is given in example 6. A few exemplary qualitative rules and design principles are given below.

Depending on the embodiments, repellent areas in the invention may be mutually organized in various ways. In some embodiments, they are organized in at least one column, and along at least one line between the emitting chamber and the receiving chamber. In many preferred embodiments, however, they are organized in at least two columns, or even preferably in at least three columns.

In other preferred embodiments, repelling areas are not organized in regular columns, but it is nevertheless advantageous, that the path from the emitting chamber to the receiving chamber, encounters several guiding tracks, and/or several repellent areas.

Thus, in some preferred embodiments, repellent areas or guiding tracks of the invention are organized in such a way, that at least one straight line drawn from the emitting chamber to the receiving chamber, crosses at least two, and preferably 3, 4 or 5 repellent areas, or crosses at least one, and preferably 2, 3, 4 or 5 guiding tracks. In said embodiment, the microfluidic device comprises at least one guiding track connecting the emitting chamber and the receiving chamber by a straight line and said at least one guiding track is connected to at least one traversing guiding track, preferably connected to 2, 3, 4, 5, or 6 traversing guiding tracks.

In other preferred embodiments, advantageously combined with the above, they are organized in at least two lines. FIGS. 4b, 4c, 4e, for instance, show examples of devices of the invention, with three columns of repellent areas. FIGS. 4a, 4e, show example of devices with two columns. FIG. 4h shows example of device of the invention, in which repellent areas are organized in several columns in the "bottom up" direction, but randomly in the left-right direction.

The organization of repellent areas within layers, or between layers, or along lines, or along columns, may also vary. Notably, the barycenters of said repellent areas may, or may not, be organized at least in part on a regular 2D lattice. In some preferred embodiments, said lattice is a square lattice. In some other embodiments, said lattice may be hexagonal, or rectangular, or in the form of lozenges, or present different levels of randomness. For instance, FIGS. 4a, 4b, involve repellent areas with barycenters organized in a rectangular lattice. FIG. 4c, 4d represent repellent areas with barycenters organized in lozenges lattice. FIGS. 4g, 4h, represent areas with barycenters organized in a non-regular, or only partly regular, lattice.

Also, the barycenters of repellent areas belonging to different layers, or to different lines or columns may be aligned along axes, or may be shifted from one layer, line or column to the other. In preferred embodiments, they are shifted. For instance, FIGS. 4a, 4b, 4c, represent designs with aligned barycenters, whereas FIG. 5d represent shifted barycenters.

In some embodiments, the shape of connecting channels or guiding structures may also comprise some other features. In some preferred embodiments, for instance, at least some of said channels or structures may present a funnel shape. In this case, the wider part of the funnel is preferably on the side of the channel or guiding structure in connection with the emitting chamber and the narrower part is preferably on the side in connection with the receiving chamber. An example of said design is presented in FIG. 2.

The width of guiding tracks may be of different sizes, but preferably they are larger than the natural width of the cell bodies to be guided. In some preferred embodiments, for studying human cells, they have a width smaller than 50 µm, preferably smaller than 30 µm, and very preferably smaller than 20 µm, or they have a width between 1 µm and 20 µm, or between 2 µm and 15 µm, or between 3 µm and 50 µm. In another embodiment, for studying multicellular organism, the guiding tracks may have a width higher than 200 µm.

In some preferred embodiments, too, the guiding tracks do not present large and abrupt changes in width, understanding that this does not preclude the possibility of having a progressive change in width, or the unavoidable change of width that occurs at the intersection of guiding tracks. So typically, in some preferred embodiments, guiding tracks do not present changes of widths of more than a factor 2, or 3, or 5, or 10, occurring on a length equal to the smallest of the two widths before and after the change, respectively, or 2, 3, 5 or 10 times said length.

Also, in some preferred embodiments, it is advantageous that the width of guiding tracks, at least some points of intersection, present a width that is at least 2, preferably at least 3, 4, 5, 7, 10, 15 or 20 times, the size of the cell bodies to be guided. For the guidance of neurites, for instance, said width is preferably at least 3, 4, 5, 7, 10, 15, 20 or 30 µm. But for other species, said width is ranging from 1 to 100 µm.

According to another embodiment, the length between the emitting chamber and the receiving chamber is ranging from 50 µm to 10 cm, preferably between 50 µm and 5 cm.

According to one embodiment, the length of a guiding track connecting the emitting chamber to the receiving chamber has a length ranging from 50 µm and 10 cm.

The invention exerts its positive action with at least two chambers connected by a network of channels or guiding tracks, but of course, in some embodiments, it may comprise more than two chambers, and notably more than two chambers connected by networks, preferably interconnected networks of guiding tracks. Also chambers may be organized in various ways, e.g. in parallel, or radially. Chambers and/or guiding tracks may also be organized in a 2D layer, or in several 2D layers, or in any 3D arrangement.

Also, in some embodiments, at least some of guiding tracks, or more generally at least some of the channels or chambers in the invention, may contain a gel medium, or medium that can be undergo a transition to a gel state.

The invention is particularly useful to manipulate, grow, select, treat, or cultivate living bodies. Therefore, it is also an object of the invention, to propose a device as described above, additionally comprising living bodies; preferably, said living bodies occupy at least one chamber, or at least one channel or guiding track.

In preferred embodiments, at least some of said living bodies are cells.

In some preferred embodiments, said cells are any of neural cells, neurons, glial cells, astrocytes, oligodendrocytes, Schwann cells or any precursor cell types allowing to obtain the types of cells mentioned above.

In some other preferred embodiments, said cells may be any of endothelial cells, epithelial cells, fibroblasts, hepatocytes, cardiomyocytes, cells from specific organs.

Said cells may be cells from any organisms. In preferred embodiments, though they are cells from mammals, and notably human cells, or cells from primates, or cells from rodents.

In some preferred embodiments, said cells are cells from cell lines.

In some other embodiments, said cells are primary cells.

In yet some particularly preferred embodiments, said cells are stem cells, or iPSC cells.

Thanks to the invention, it is possible to perform on cells or with cells different types of operations that could not be done, or could not be done as efficiently, in prior art devices. Thus, it is also an object of the invention, to propose an Instrument for culturing cells, for screening biological or chemical species, notably drugs, and thus instruments for, as a non-limiting list of examples, drug discovery, drug testing, stem cells growth, stem cells differentiation, stem cells culture, stem cells production, cancer research, for medicine, biotechnology, life sciences, food industry, environment screening, and others, said instrument comprising a minifluidic device of the invention as describe above.

Thanks to its possibility to better control cell shapes than in prior art the invention also proposes Implantable devices, with at least some of the characteristics describe above. Said implantable devices may be, as a non-limiting list, devices for the regeneration of parts of the nervous system, for the improvement of various types of handicap, notably impairment of motor or sensor functions. In other embodiments, said implantable device may be a component of an epithelium, of an endothelium, of a vascular system, of an organ.

Of course, besides the minifluidic device, or chip comprising chambers and networks of channels or guiding tracks as described above, instruments or devices of the invention may comprise any kind of additional elements known in the art of cell culture, biological studies, medicine, microscopy, instrumentation or microfluidics, such as imaging components, optical components, magnetic components, acoustic components, mechanical components, flow control components, reservoirs, incubators, microscopes, chip holders, micromanipulators, electric components, computers, software, and the like.

As mentioned above, the invention is particularly interesting for controlling the motion, the shape, or the position of living bodies.

It is thus another object of the invention, to propose a method for controlling the motion, the shape, the deformation, the growth the spatial orientation, or the position of living bodies, said method comprising a step of placing said living body inside a minifluidic device of the invention.

In other embodiments, the invention also proposes a method for any of culturing cells, for screening biological or chemical species, for drug discovery, drug testing, stem cells growth, stem cells differentiation, stem cells culture, stem cells production, cancer research, for medicine, biotechnology, life sciences, food industry, environment screening, comprising a step of cultivating living bodies in a device of the invention.

One object of the invention is a device comprising a first chamber and a second chamber linked by a network of at least three guiding tracks, wherein at least a first guiding track is connected to the first chamber and at least a second guiding track is connected to the second chamber, the at least first and second guiding tracks are connected to each other with at least a third guiding tracks, wherein the at least three guiding tracks when intersecting form an object with a proximal end substantially oriented toward the first chamber and a distal end substantially oriented toward the second chamber, wherein the proximal end comprises at least one internal angle from 150° to 180° and wherein the distal end comprises at least one internal angle of less than 150° (FIG. 4a to f).

According to one embodiment, said device comprises at least two objects formed by the guiding tracks intersection, with a proximal end substantially oriented toward the first chamber and a distal end substantially oriented toward the second chamber, wherein the proximal end comprises at least one internal angle from 150° to 180° and wherein the distal end comprises at least one internal angle of less than 150°, and the distal end of the second object is separated from the proximal end of the first object by a guiding track.

According to one embodiment, the length of an object is ranging from 20 μm to 10 mm.

One object of the invention is a device comprising a first chamber and a second chamber linked by a network of at least four guiding tracks, wherein at least a first guiding track is connected to the first chamber and at least a second guiding track is connected to the second chamber, the at least first and second guiding tracks are connected to each other by at least a third and a fourth guiding tracks, wherein the at least four guiding tracks when intersecting form an object with a proximal end substantially oriented toward the first chamber and a distal end substantially oriented toward the second chamber, wherein the proximal end comprises at least one internal angle from 150° to 180° and wherein the distal end comprises at least one internal angle of less than 150° (FIGS. 4i and j).

According to an embodiment of the invention, the proximal end comprises at least one internal angle from 150°, 155°, 160°, 165°, 170° or 175° to 180°.

According to an embodiment of the invention, the distal end comprises at least one internal angle of less than 150°, 145°, 140°, 135°, 130°, 125°, 120°, 115°, 110°, 105°, 100°, 95°, 90°, 85°, 80°, 75°, 70°, 65°, 60°, 55°, 50°, 45°, 40°, 35°, 30°, 25°, 20°, 15°, 10°.

According to an embodiment of the invention, the proximal end is a convex hemicylinder or fraction thereof. According to an embodiment of the invention, the proximal end has a convex hemicircular or semielliptical form or a fraction thereof. According to an embodiment of the invention, the proximal end has a convex polyhedral or polygonal form.

According to an embodiment of the invention, the distal end is a concave hemicylinder fraction thereof. According to an embodiment of the invention, the distal end has a concave hemicircular or semielliptical form or a fraction thereof. According to an embodiment of the invention, the distal end has a concave polyhedral or polygonal form.

According to an embodiment of the invention, the device described above is combined with the device described in the patent application PCT/FR09/01198, herein incorporated by reference.

According to an embodiment of the invention, the guiding tracks have a decreasing width from the end of the first chamber to the beginning of the second chamber.

According to an embodiment of the invention, the decreasing width of the guiding tracks is linear.

According to an embodiment of the invention, the decreasing width of the guiding tracks is exponential.

According to an embodiment of the invention, the decreasing width of the guiding tracks is according to a power function with a negative exponent.

According to an embodiment, the width of the guiding tracks from the end of the first chamber to the beginning of the second chamber is comprised between 10 to 50 micrometers.

According to an embodiment, the width of the guiding tracks from the end of the first chamber to the beginning of the second chamber is comprised between 10 to 40 micrometers.

According to an embodiment, the width of the guiding tracks from the end of the first chamber to the beginning of the second chamber is comprised between 10 to 30 micrometers.

According to an embodiment, the width of the guiding tracks from the end of the first chamber to the beginning of the second chamber is comprised between 10 to 20 micrometers.

According to an embodiment, the width of the guiding tracks from the end of the first chamber to the beginning of the second chamber is about 15 micrometers.

According to an embodiment of the invention, the guiding tracks have an increasing width from the end of the second chamber to the beginning of the first chamber.

According to an embodiment, the increasing width of the guiding tracks is linear.

According to an embodiment, the increasing width of the guiding tracks is exponential.

According to an embodiment, the increasing width of the guiding tracks is according to a power function with a positive exponent.

According to an embodiment, the width of the guiding tracks from the end of the second chamber to the beginning of the first chamber is comprised between 10 to 50 micrometers.

According to an embodiment, the width of the guiding tracks from the end of the second chamber to the beginning of the first chamber is comprised between 10 to 40 micrometers.

According to an embodiment, the width of the guiding tracks from the end of the second chamber to the beginning of the first chamber is comprised between 10 to 30 micrometers.

According to an embodiment, the width of the guiding tracks from the end of the second chamber to the beginning of the first chamber is comprised between 10 to 20 micrometers.

According to an embodiment, the width of the guiding tracks from the end of the second chamber to the beginning of the first chamber is about 15 micrometers.

According to an embodiment of the invention, the guiding tracks have a decreasing width from the proximal end to the distal end.

According to an embodiment, the decreasing width of the guiding tracks is linear.

According to an embodiment, the decreasing width of the guiding tracks is exponential.

According to an embodiment, the decreasing width of the guiding tracks is according to a power function with a negative exponent.

According to one embodiment, the width of the guiding tracks from the proximal end to the distal end is comprised between 10 to 300 micrometers.

According to an embodiment, the width of the guiding tracks from the proximal end to the distal end is comprised between 10 to 50 micrometers.

According to an embodiment, the width of the guiding tracks from the proximal end to the distal end is comprised between 10 to 40 micrometers.

According to an embodiment, the width of the guiding tracks from the proximal end to the distal end is comprised between 10 to 30 micrometers.

According to an embodiment, the width of the guiding tracks from the proximal end to the distal end is comprised between 10 to 20 micrometers.

According to an embodiment, the width of the guiding tracks from the proximal end to the distal end is about 15 micrometers.

According to an embodiment of the invention, the guiding tracks have an increasing width from the distal end to proximal end.

According to an embodiment of the invention, the increasing width of the guiding tracks is linear.

According to an embodiment of the invention, the increasing width of the guiding tracks is exponential.

According to an embodiment of the invention, the increasing width of the guiding tracks is according to a power function with a positive exponent.

According to an embodiment, the width of the guiding tracks from the distal end to proximal end is comprised between 10 to 50 micrometers.

According to an embodiment, the width of the guiding tracks from the distal end to proximal end is comprised between 10 to 40 micrometers.

According to an embodiment, the width of the guiding tracks from the distal end to proximal end is comprised between 10 to 30 micrometers.

According to an embodiment, the width of the guiding tracks from the distal end to proximal end is comprised between 10 to 20 micrometers.

According to an embodiment, the width of the guiding tracks from the distal end to proximal end is about 15 micrometers.

According to an embodiment of the invention, the width of the object is comprised between 10 to 200 micrometers.

According to an embodiment of the invention, the width of the object is comprised between 50 to 150 micrometers.

According to an embodiment of the invention, the width of the object is from 60, 70, 80, 90, 100, 110, 120, 130, 140, to 150 micrometers.

According to an embodiment, the width of the object can vary linearly or exponentially or according to a power function with a positive or negative exponent.

According to one embodiment, the width of the objects is ranging from 2 times the width of the device to 50 times the width of the device.

According to one embodiment, the width of the objects is ranging from 3 times the width of the device to 20 times the width of the device.

According to an embodiment of the invention, the length of the object is from 10 to 200 micrometers.

According to an embodiment of the invention, the length of the object is from 50 to 150 micrometers.

According to an embodiment of the invention, the length of the object is from 60, 70, 80, 90, 100, 110, 120, 130, 140, to 150 micrometers.

According to an embodiment of the invention, the height of the object is from 1 to 10 micrometers.

Another object of the invention is a device comprising a first chamber and at least one second chamber connected by at least one guiding track, wherein the height of the wall of the second chamber connected to the guiding track is higher than the height of the guiding track and the guiding track is connected to the second chamber at a position in the wall of the second chamber with its bottom above the bottom of the second chamber (FIGS. 8B, C, D) preferably, the vertical distance from the bottom of the guiding track to the bottom of the chamber is at least 5 µm, and preferably at least 10 µm, and very preferably at least 20 µm.

BRIEF DESCRIPTION OF THE DRAWINGS

FIG. 4 represents a non-limitative series of examples of possible embodiments of the invention.

FIG. 4a represents a first possible design, comprising a first chamber 1, called emitting chamber, a second chamber 2, called receiving chamber, repellent areas 3, separated by guiding tracks 4 organized in two lines and two columns (additional lines, not represented, may extend beyond the dashed lines). Interconnections between guiding tracks 5 are here 4-ways interconnections. In this design, the right column of repellent areas has two cusps on the side facing the receiving chamber, and no cusp on the side facing the emitting chamber. The left column has two cusps on both sides, but the cusps facing the receiving chamber are sharper than the cusps facing the emitting chamber. The network of guiding tracks is a fully interconnected one.

FIG. 4b represents a second design, with three columns of repellent areas. The right and left columns are identical to those of FIG. 4a, the center column has two sharp cusps on the side facing the receiving chamber, and no cusp on the side facing the emitting chamber.

FIG. 4c represents another possible design, in which the center column of repellent areas has one cusp on the side facing the receiving chamber, and no cusp on the side facing the emitting chamber. The guiding track at the left of said repellent areas is rounded and has its concave part facing the receiving chamber.

FIG. 4d represents another design, in which repellent areas are not organized in regular columns. In that case, interconnections 5 are 3-ways interconnections.

FIG. 4e represents yet another design, with three columns of repellent areas according to the invention, combined with funnel-shaped guiding tracks 4.

FIG. 4f represents another design, showing a preferred embodiment, in which the boundary between the repelling areas and the chambers is not straight.

FIG. 4g represents yet another embodiment, in which the size of repellent areas is not uniform along one direction.

FIG. 4h represents another embodiment, in which the size of repellent areas is not uniform along two directions.

FIG. 4i represents another embodiment, in which the network of guiding tracks is not fully interconnected. This embodiment comprises at least one connection of said network with the emitting chamber, and one connection with the receiving chamber. It also comprises two repellent areas 3 with one cusp facing the receiving chamber, and no cusp facing the emitting chamber. It also comprises 5 guiding tracks 4 and two 4-ways interconnections between said guiding tracks 5. Of course this design can be repeated any number of times as desired, laterally, in order to create several independent lines of interconnections between the emitting and the receiving chamber, or longitudinally, as represented in FIG. 4j, in order to create several columns of guiding tracks and repellent areas. The latter design is interesting for instance to increase the selectivity of the design.

FIG. 4j represents another embodiment, in which the network of guiding tracks corresponds to an example of repeated design of FIG. 4i.

FIG. 5 represents as another example, a zoom on a part of a positive mold for preparing particular realization of a device according to a design combining repellent areas of the invention (only the center column is shown fully), and some microchannels with a funnel shape, wherein the guiding tracks are constituted by microchannels or trenches.

FIG. 6 exemplifies the use of the invention, to facilitate growth of axons from the emitting chamber to the receiving chamber (FIG. 6A and FIG. 6B) and to prevent growth of axons from the receiving chamber to the emitting chamber (FIG. 6C and FIG. 6D).

FIG. 7 represents a comparison between experiments and theoretical model, for the operation of the invention, and an evaluation of the selectivity of different designs.

FIG. 7B shows the comparison between experimental results (top) and simulation results (bottom) for a design of the invention similar to 4a.

FIG. 8 represents embodiments of the invention in which the characterizing features are developed in a third dimension.

REFERENCES

1—Emitting chamber;
2—Receiving chamber;
3—Repellent areas or Object;

4—Guiding tracks;
5—Interconnections between guiding tracks;
6—Third chamber.

EXAMPLES

The present invention is further illustrated by the following examples.

Example 1

Figure 1:
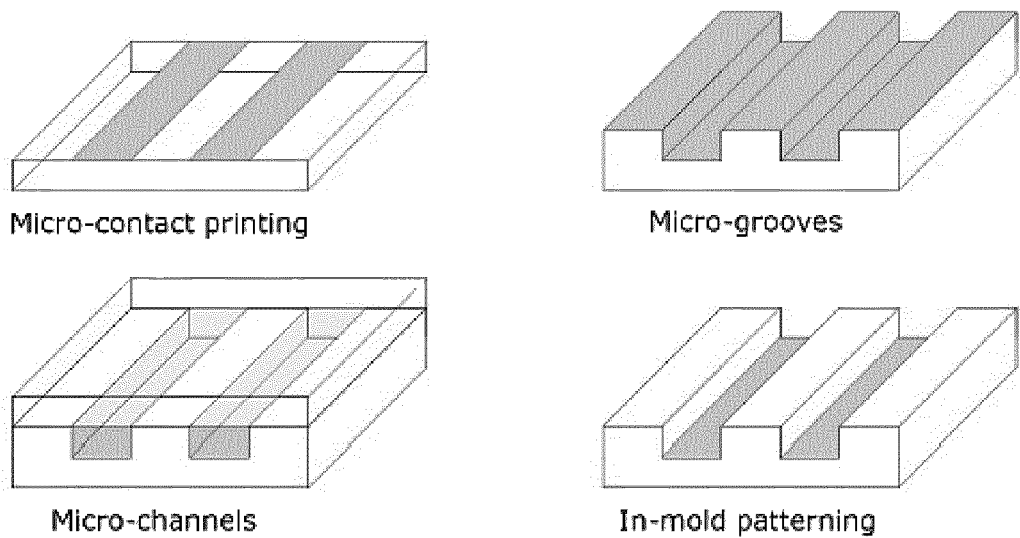
FIG. 1 illustrates different types of guiding cues usable to create guiding patterns.

Examples of different types of guiding cues, as shown in FIG. 1, and of methods of prior art for the preparation of guiding patterns of the of the chemical type (surface treatment), of the physical type (microgrooves, microchannels), or of a type combining physical and chemical guiding cues (in mold patterning). The grey surfaces are FIG. 1 represent accessible areas while the white surfaces are inaccessible/repellent areas.

Creation of surface based guiding patterns (FIG. 1a) can be performed e.g. by microcontact printing, as in Offenhäusser A, et al. Soft Matter. 2007; 3:290-8. Microgrooves or microchannels (FIG. 1b, 1c) can be prepared e.g. by conventional techniques of soft lithography, by molding a polymer such as silicone (PDMS) upon a master, as described e.g. in Park J, et al. J Neurosci Methods. 2014; 221:166-74. The hybrid in mold patterning technique (FIG. 1d), finally, can be performed as described e.g. in Zhang J, et al. Biomaterials. 2006; 27:5734-9.

Example 2

Figure 2:
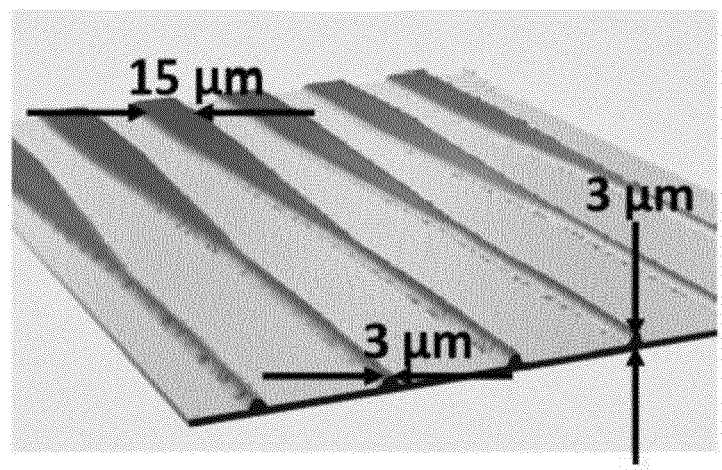
FIG. 2 displays different types of guiding patterns of prior art.

Example of designs of guiding patterns of prior art.
The guiding patterns presented in the following examples can refer indifferently to different patterning methods of prior art, as presented in FIG. 1, including guiding patterns of chemical nature (surface treatment), physical nature (microgrooves, microchannels), or of a combination of physical and chemical guiding cues (in-mold patterning). Various designs were presented e.g. in WO 2010040920 to Peyrin (FIG. 2A). among those, funnel shaped microchannels, such as represented in FIG. 2B, were used to produce directional filtering of axonal growth, using the higher probability of entry of the cell bodies (in particular, axons) into the wider entrance (here 15 μm wide) compared to the one for the narrower entrance (only 3 μm wide). However, making such tapered channels requires high resolution, hence costly microfabrication means, and the narrowing of the tracks in some embodiments can have harmful effects on axons or other cell bodies, and impair diffusion between the chambers.

Example 3

Figure 3A:
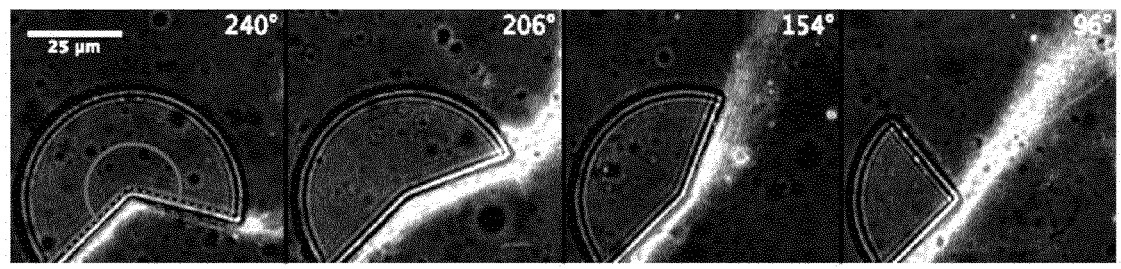
FIG. 3 represents an investigation of the behavior of axons encountering cusps (FIG. 3A), and an example of a device of the invention (FIG. 3B), with neuron connection allowed from left to right.
Figure 3B:
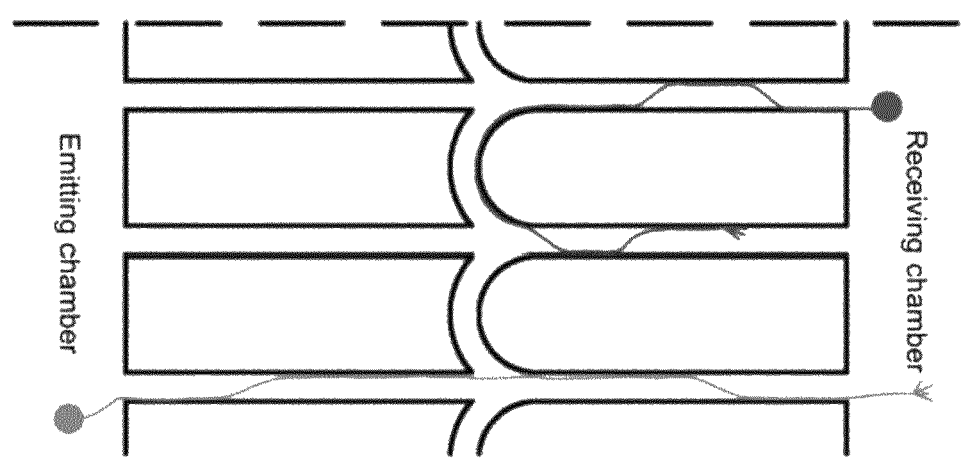

Examples of designs of devices of the invention.
In the devices of the present invention, in contrast, selectivity can be obtained without any channel narrowing, avoiding the above disadvantages. FIG. 3A demonstrates a surprising property of axons, here evidenced by immunostaining of beta-tubulin, to follow preferentially the edges of guiding patterns provided these edges deviate away from the growth direction at a rate low enough. In particular, axons can follow the edges of structures even along cusps with angles smaller than 180° up to a certain critical angle (here between 154° and 96°). FIG. 3B shows an example of guiding patterns exploiting the edge affinity of axons to produce directional connectivity between neurons, from the emitting chamber to the receiving chamber, and the typical behavior of axons is such guiding patterns. Depending on whether they are growing from the emitting chamber or the receiving chamber, these axons behave differently at the interconnections: they tend to go straight when they encounter the interconnection from the side with sharp cusps, whereas they tend to follow the edges and make U-turns when they meet the interconnection from the side with round edges.

Other examples of guiding patterns exploiting the property of edge affinity in order to create asymmetrical connectivity include those presented in FIG. 4.

Example 4

Mold for the preparation of device of the invention.
FIG. 5 shows the profilometric rendering of a mold that can be used to prepare a device of the invention, in which the guiding tracks are physical, i.e. grooves or microchannels, as described in Example 1. The mold is prepared by photolithography on SU-8 coated silicium wafer following the SU-8 guidelines from Microchem. From this mold, devices of the invention, for instance in PDMS, can be cast, cured, and removed from the mold. The PDMS parts can be sealed with a glass slide through plasma bonding in order to create microchannels, or used directly as micro-grooves. A negative of this mold can also be used to create stamps for micro-contact printing and in-mold patterning (FIG. 1).

In this particular embodiment, the center column (other columns are not shown in full) comprises two cusps on the side facing the receiving chamber, and no cusp facing the emitting chamber. The channels or grooves separating the repellent areas in the center columns additionally have a funnel shape, similar to those described in FIG. 4E. The largest channels (lower left) have a width of 15 μm, and the smallest channels (upper right) have a width of 2 μm.

Example 5

Device of the invention used to control axonal growth in vitro.
FIG. 6 shows a particular embodiment where the guiding patterns are PDMS microchannels similar to those described in FIG. 4d, with two columns of repellent areas. In this particular embodiment, the guiding tracks have a width of 10 um and the distance between the two chambers (at the left and right of the image, respectively, is 1 mm. The device was seeded with primary cortical neurons from mice embryos either on the emitting chamber or the receiving chamber, and they were allowed to grow axons for 9 days in vitro (DIV) inside the guiding patterns. Neurons were transfected at 7 DIV with a GFP expressing plasmid using lipofectamine 3000 (Invitrogen) so as to yield a small fraction of fluorescent neurons. The device was observed both in Differential Interference Contrast (DIC) and fluorescence microscopy using the appropriate filter set. FIGS. 6A and 6B show respectively DIC and fluorescence images of a same region of the device, where neurons were seeded in the emitting chamber. FIGS. 6C and 6D are for a region where neurons were seeded in the receiving chamber at the same density. As it can be seen on the DIC images, the number of axons growing to the opposite chamber is larger when neurons are seeded in the emitting chamber. This can be attributed to the paths taken by individual axons at the junctions, which are clearly visible in fluorescence imaging.

Example 6

Theoretical model useful for the design and optimization of the invention.

A model was designed to simulate axons growing on an environment map by adding iteratively new segments in the appropriate direction. The deviation from previous growth direction is drawn at each time step from a probability density function defined on [−pi,pi] that takes into account the persistence length of axons, and the affinity of axons for edges and other axons. All these parameters were fitted from experimental observation.

Figure 7A:
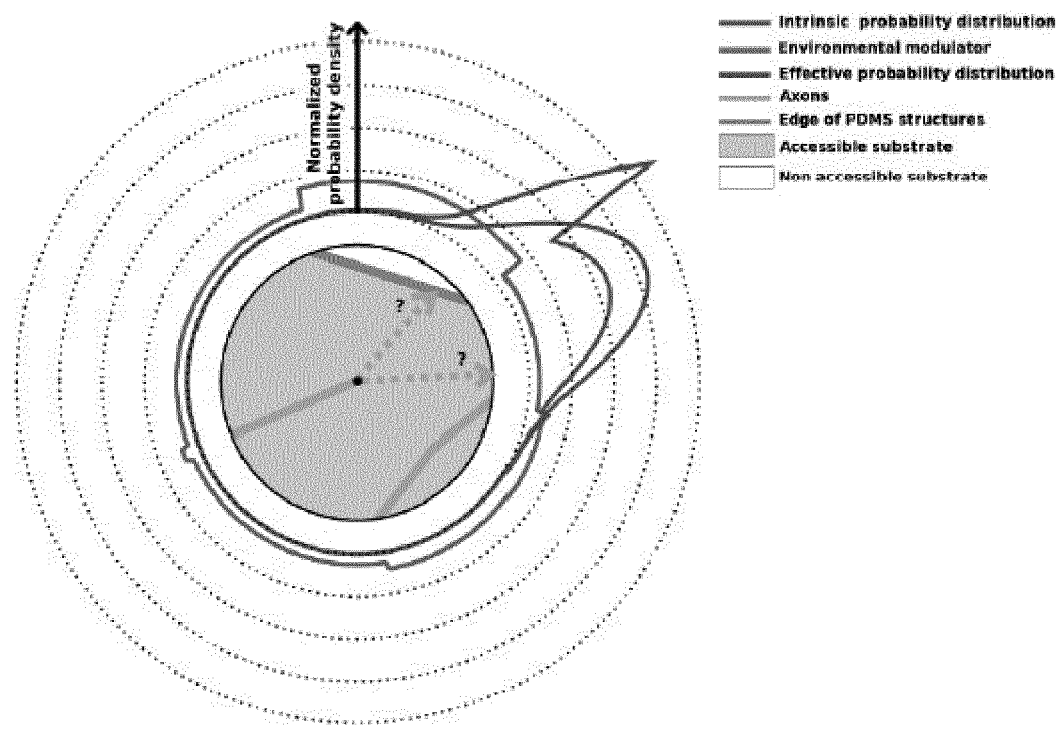
FIG. 7A shows the effective probability distribution.
Figure 7B:
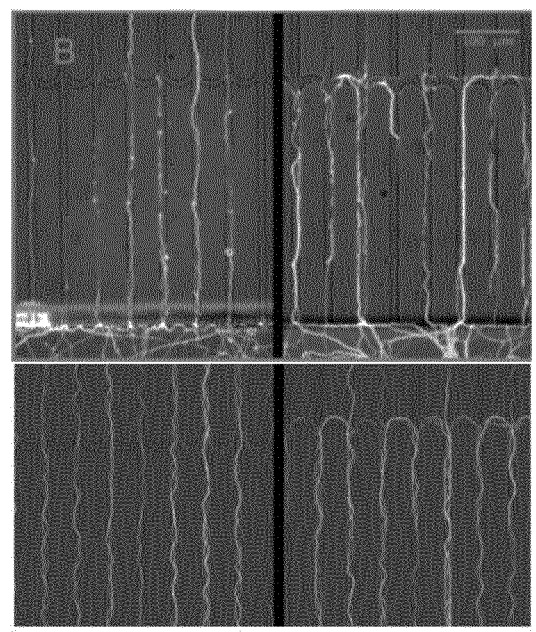
Figure 7C:
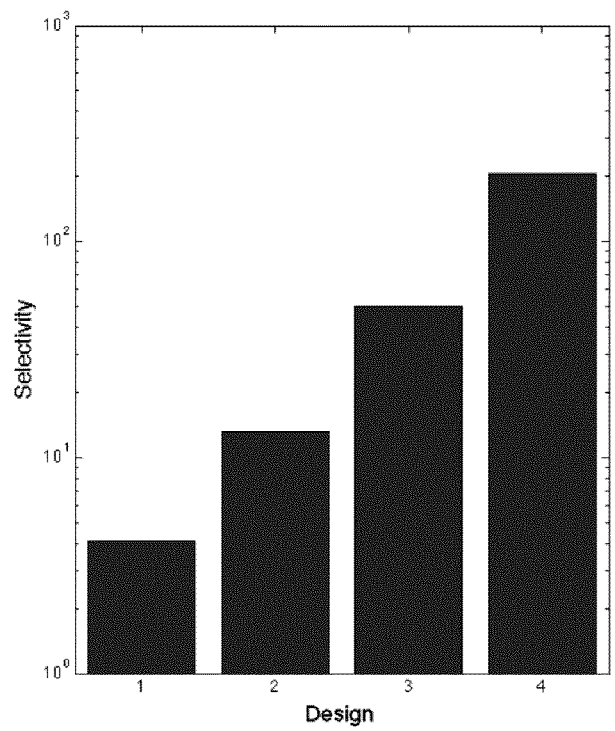
FIG. 7C presents the theoretical selectivity (number of axons crossing the guiding patterns from the emitting to the receiving chambers over the number of axons crossing the guiding patterns in the reverse direction) of a few different designs. Designs 1, 2 and 3 have guiding patterns similar to 4f, with respectively 2, 5 and 10 columns of repellent areas. Design 4 has guiding patterns similar to 4e, with 5 columns of repellent areas.

This density function is firstly determined by intrinsic growth parameters reflecting the characteristic persistence length of freely growing axons. It is then affected by an environmental modulator accounting for the accessibility of different areas in the pixel map (1 for accessible pixels, 0 for inaccessible pixels). Additionally, the edges and axons appear as special pixel values on the environment map. The environmental modulator function is obtained by probing the substrate around the axon tip in all directions. For each direction, the value of the environmental modulator is the maximal pixel value along this direction on the environment map, and within a distance d from the tip (or before, if an inaccessible area is met). The effective probability distribution is finally obtained by multiplying the intrinsic probability distribution with the environmental modulator and normalizing the result (FIGS. 7A, B and C).

This model represents a tool useful for designing new embodiments, or to optimize an existing embodiment, by an educated process. For instance, a first particular design of embodiments, or a few such designs, may be constructed and used to optimize the parameters of the model, for instance relative to a given type of living bodies. Then, the model with these parameters can be applied to other designs of embodiments, and help to anticipate their performance, without having to perform experiments for all possible designs. However, this model may not work in all cases, for instance it may not work work for some other living bodies than axons, and it is not intended to represent a certain explanation of the mode of operation of the invention, or the only way by which the invention exerts its advantages. Thus this model should not be viewed in any way as a means for defining or restricting the field of the invention, which can be used without this model, and indeed may in some embodiments yield results not fitting to this model.

Example 7

Example of embodiments comprising cusp asymmetries in a plane perpendicular to the main plane of the device.

FIGS. 8 a-d represent different devices in 3D view (top) and along a vertical cut, perpendicular to the main plain of the device (bottom). All devices comprise a first emitting chamber 1, a second receiving chamber 2, and a guiding track 3, here in the form of a microchannel (the device may advantageously comprise a multiplicity of said microchannels in parallel between the two chambers, a single channel is represented here only for convenience). The bottom of the microchannel and the bottom of the chambers present a surface treated by polylysin or fibronectin, in order to favour the adhesion of neurons.

Figure 8A:
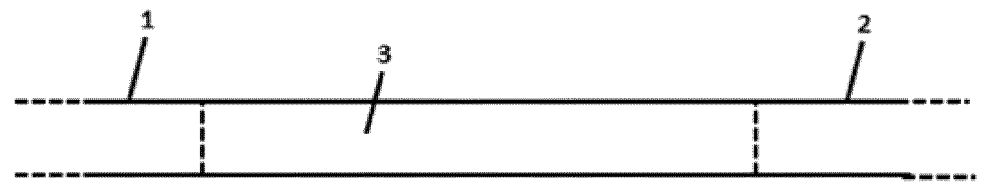
FIG. 8A represents a device of prior art, with no cusp in the vertical plane B B'.

According to FIG. 8a apparatus, axons will travel easily from the emitting chamber to the receiving chamber, but they will be hindered to enter the microchannel from the receiving chamber, due to the presence of the cusp.

Figure 8B:
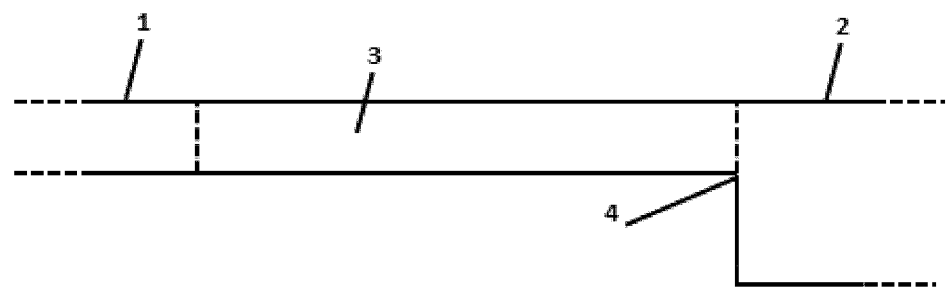
FIG. 8B represents a device of the invention, comprising a cusp 4 in the BB' plane at the extremity of the microchannel 3, on the side of the receiving chamber 2, and no such cusp at the extremity of said channel on the side of the emitting chamber 1.
Figure 8C:
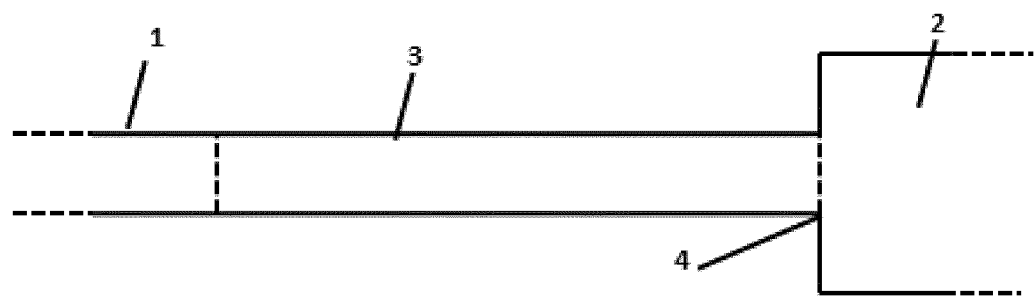
FIG. 8C represents another device of the invention, comprising two cusps 4 in the BB' plane at the extremity of the microchannel 3, on the side of the receiving chamber 2, and no such cusp at the extremity of said channel on the side of the emitting chamber 1.
Figure 8D:
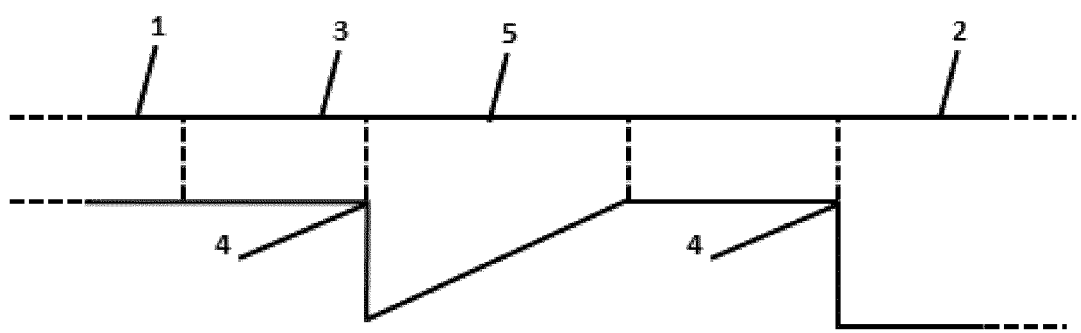
FIG. 8D represents another device of the invention, comprising two cusps 4 in the BB' plane at the extremity of the microchannels 3, on the side of the receiving chambers 6 and 2.
Figure 8E:
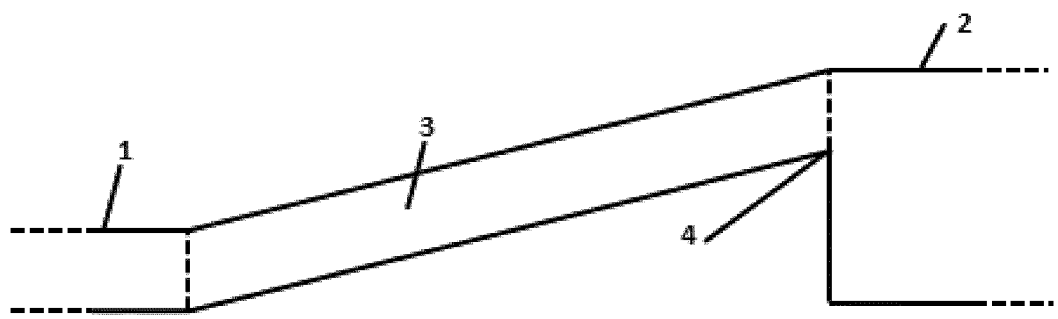
FIG. 8E represents a device of the invention, comprising a cusp 4 in the BB' plane at the extremity of the microchannel 3, on the side of the receiving chamber 2, and no such cusp at the extremity of said channel on the side of the emitting chamber 1, and the receiving chamber is higher than the emitting chamber 2.
Figure 9:
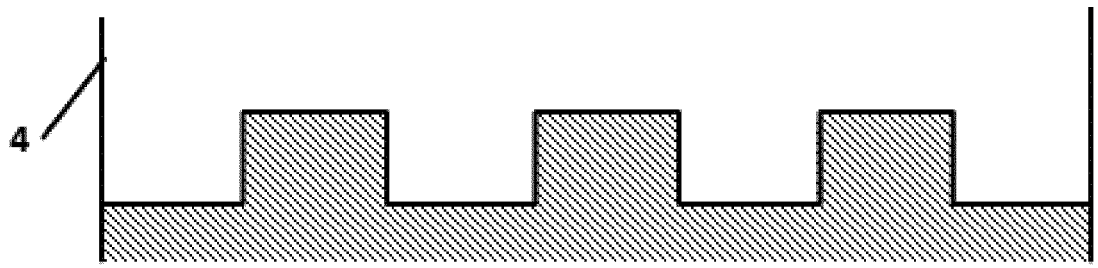
FIG. 9 represents one guiding track (4) according to an embodiment of the present invention, wherein the guiding track (4) comprises one or several micro-cuts for guiding living bodies.

The guiding tracks with not in plane cusps, as described above, may also be combined or chained, in order to constitute more efficient networks. For instance, FIG. 8d represents another device of the invention, in which a design similar to that of FIG. 8b, is repeated along the path between an emitting chamber 1 to a receiving chamber 6, across an intermediate chamber 6.

The invention claimed is:

1. A microfluidic device to manipulate, select, treat, or cultivate living bodies, comprising:
   a first chamber;
   a second chamber;
   a network of guiding tracks located between the first chamber and the second chamber, the network of guiding tracks comprising a first guiding track extending between and connecting the first chamber and the second chamber and a second guiding track extending between and connecting the first guiding track with at least two interconnections, the second guiding track comprising a curved part, the curved part exhibiting a concavity facing the second chamber or a part of the network of guiding tracks connected to the second chamber, and
   repellent areas or repellent volumes located between the first chamber and the second chamber and defining the network of guiding tracks, the repellent areas or repellent volumes having an affinity to support growth or adhesion of living bodies that is less than an affinity of the network of guiding tracks and of the first and second chambers to support the growth or adhesion of living bodies,
      wherein the network of guiding tracks defined by the repellent areas or repellent volumes is shaped such that the network of guiding tracks is asymmetrical relative to a lateral axis extending perpendicular to a longitudinal axis of the microfluidic device, the longitudinal axis extending between the first chamber and the second chamber, the lateral axis located intermediately along a longitudinal dimension of the network of guiding tracks; and
      wherein at least one of the repellent areas or repellent volumes comprises a first side in contact with or facing the second chamber and a second side in contact with or facing the first chamber, wherein:
         the first side has at least one cusp having a tip angle, and
         the second side has no or fewer cusps than the first side and/or the second side has at least one cusp, the at least one cusp of the second side having a tip angle that is greater than the tip angle of the at least one cusp of the first side.

2. The microfluidic device according to claim 1, wherein the network of guiding tracks comprises at least two first guiding tracks connecting the first chamber and the second chamber, and wherein each first guiding track comprises at least one interconnection with the second guiding track.

3. The microfluidic device according to claim 1, wherein the first guiding track comprises at least two interconnections with the second guiding track.

4. The microfluidic device according to claim 1, wherein the network of guiding tracks comprises at least two second guiding tracks, and wherein each second guiding track connects the first guiding track with at least two interconnections.

5. The microfluidic device according to claim 4, wherein the first guiding track is connected to at least two second guiding tracks.

6. The microfluidic device according to claim 1, wherein each interconnection is a 3-way interconnection.

7. The microfluidic device according to claim 1, wherein each internal angle between the first guiding track and the second guiding track and facing the second chamber or a part of the network of guiding tracks connected to the second chamber ranges from 90° to 180°, from 100° to 180°, from 120° to 180°, from 150° to 180°, from 160° to 180° or from 170° to 180°.

8. The microfluidic device according to claim 1, wherein each internal angle between the first guiding track and the second guiding track and facing the first chamber or a part of the network of guiding tracks connected to the first chamber is smaller than 150°, 140°, 130°, 120°, 110°, 100° or 90°.

9. The microfluidic device according to claim 1, wherein the space between two adjacent interconnections along the first guiding track ranges from 20 μm to 5 mm.

10. The microfluidic device according to claim 1, wherein each of the first chamber and the second chamber comprises a bottom and wherein:
   the first guiding track is connected to the first chamber at a level of the bottom of the first chamber; and
   the first guiding track is connected to the second chamber at a level higher than the level of the bottom of the second chamber so as to form a step between the bottom of the second chamber and the first guiding track.

11. The microfluidic device according to claim 10, further comprising a third chamber connected to the second chamber by the second guiding track.

12. The microfluidic device according to claim 11, wherein the third chamber comprises a bottom and wherein:
   the second guiding track is connected to the second chamber at the level of the bottom of the second chamber; and
   the second guiding track is connected to the third chamber at a level higher than the level of the bottom of the third chamber so as to form a step between the bottom of the third chamber and the second guiding track.

13. The microfluidic device according to claim 10, wherein at least one of the first guiding track and the second guiding track comprises at least one micro-cut thereon.

14. The microfluidic device according to claim 10, wherein the bottom of the second chamber is not parallel with the bottom of the first chamber.

15. The microfluidic device of claim 1, wherein the first guiding track extends between two laterally adjacent repellent areas or repellent volumes; and wherein the second guiding track extends between two longitudinally adjacent repellent areas or repellent volumes.

16. The microfluidic device of claim 1, wherein the at least one cusp of the first side of the repellent area or repellent volume is located at an intersection of the first guiding track and the second guiding track.

17. The microfluidic device of claim 1, wherein when the second side of the repellent area or repellent volumes comprises at least one cusp, the at least one cusp is located at an intersection of the first guiding track and the second guiding track.

18. A method to manipulate, select, treat, or cultivate living bodies, comprising the following steps:
   providing the microfluidic device according to claim 1;
   cultivating at least one living body in the first chamber and cultivating at least one living body in the second chamber;
   guiding the at least one living body from the first chamber to the second chamber without guiding the living body from the second chamber to the first chamber.

19. The method according to claim 18, wherein the at least one living body in the first chamber and the at least one living body in the second chamber are cells, neurites, axons, dendrites, invadopodia, filipodia, cell membranes, cellular protrusions, flagella, microtentacles, growth cones, glial cells, fungi, plant cells, filamentous fungies, whole organisms, worms, yeasts, myxomycetes, animal cells, multicellular spheroids, organoids, or embryos.

* * * * *